United States Patent [19]
Hirschy et al.

[11] 4,136,126
[45] Jan. 23, 1979

[54] PREPARATION OF β-PHELLANDRENE

[75] Inventors: Linda M. Hirschy, Jacksonville; Bernard J. Kane, Atlantic Beach; Sean G. Traynor, Jacksonville, all of Fla.

[73] Assignee: SCM Corporation, New York, N.Y.

[21] Appl. No.: 886,659

[22] Filed: Mar. 15, 1978

[51] Int. Cl.² ................................................ C07C 1/22
[52] U.S. Cl. .................................. 260/666 A; 252/522
[58] Field of Search ................................... 260/666 A

[56] References Cited

U.S. PATENT DOCUMENTS

| | | | |
|---|---|---|---|
| 2,922,829 | 1/1960 | Bottoms | 260/666 A |
| 2,922,830 | 1/1960 | Bottoms | 260/666 A |
| 3,146,271 | 8/1964 | Louthau | 260/666 A |
| 3,185,743 | 5/1965 | La Combe et al. | 260/666 A |
| 3,280,202 | 10/1966 | Gilch | 260/666 A |

*Primary Examiner*—Veronica O'Keefe
*Attorney, Agent, or Firm*—Jerry K. Mueller, Jr.

[57] ABSTRACT

β-Phellandrene is prepared by pyrolyzing a para-menth-1-ene-7-sulfonate salt.

11 Claims, No Drawings

PREPARATION OF β-PHELLANDRENE

BACKGROUND OF THE INVENTION

The present invention relates to β-phellandrene and more particularly to a novel process for its preparation.

β-Phellandrene (1-methylene-4-isopropyl-2-cyclohexene) is widely used in perfumes and artificial essential oils because of its peppery, minty, refreshing, and slightly citrusy odor. Also, β-phellandrene finds importance as an intermediate in various synthesis schemes, such as in the preparation of 1-menthol. However, it has been difficult to synthesize β-phellandrene in good yields, such as from paramenthadienes, because of its ease in isomerizing under most reaction conditions to its α-phellandrene and α-terpinene isomers. The present invention provides a method for synthesizing β-phellandrene in good chemical and optical yields.

SUMMARY OF THE INVENTION

The present invention is a process for making β-phellandrene. Such process comprises heating a para-menth-1-ene-7-sulfonate salt at a temperature of about 150° to about 350° C under non-acidic conditions until the β-phellandrene product is formed.

DETAILED DESCRIPTION OF THE INVENTION

The feed for the present process is para-menth-1-ene-7-sulfonate salt. One method for preparing such sulfonate salt involves the reaction of β-pinene and a bisulfite, such as sodium bisulfite, under free radical conditions to obtain the paramenth-1-ene-7-sulfonate salt. Such method for preparing sulfonate salts can be found in commonly-assigned application Ser. No. 879,127, filed Feb. 21, 1978, of Sean G. Traynor and Bernard J. Kane, the disclosure of which is incorporated herein by reference. Another method for preparing the sulfonate salts involves the reaction of a thiol with β-pinene in the presence of a peroxy catalyst (e.g. di-t-butyl peroxide) as proposed by Gaiffe and Castanet in *C. R. Acad. Soc. Paris*, Vol. 271, Series C, pp. 1012–1014 (1970). The para-menth-1-ene-7 thiols then can be conventionally oxidized to a sulfonic acid, and the sulfonic acid converted into its salt. Of course, any other suitable means for preparation of the para-menth-1-ene-7-sulfonate salt can be used to provide a feed stock suitable for admission to the present process.

Depending upon the particular method chosen for preparing the sulfonate salt, such sulfonate salt can be a salt of an alkali metal, an alkaline earth metal, ammonia, an amine (such as triethanolamine), aluminum, zinc or the like. For economy, the sulfonate salt suitably will be an alkali metal sulfonate salt, particularly a sodium or potassium salt. Most methods for preparing the sulfonate salt provide the salt as a hydrate. The present invention applied equally to the unhydrated as well as the hydrated sulfonate salt.

In practicing the present invention, the para-menth-1-ene-7-sulfonate salt (mono hydrate typically) is charged into a reaction vessel and is pyrolyzed at a temperature of from about 150° to about 350° C or higher. Solvents such as water or a non-participating organic solvent may be used as is necessary, desirable, or convenient. While the sulfonate salt preferably is pyrolyzed under reduced pressure, atmospheric or even a slight superatmospheric pressure may be employed. Reduced pressure pyrolysis of the sulfonate salt is preferred for distilling the β-phellandrene product and the released water of hydration from the reaction mixture which distillation is favorable for pushing the reaction conversion more to the desired product. Under reduced pressure and higher temperatures of about 250° to 350° C, the reaction is completed in about 15 minutes. Generally, reaction times for making the β-phellandrene product will range from a few minutes on up to an hour or longer.

The present process is unique in that good chemical and optical yields of the β-phellandrene result from the process. This is somewhat surprising in that β-phellandrene is known to rapidly isomerize to its double bond isomers quite readily. The β-phellandrene product typically will be recovered in at least about 80% to 90% purity from the process and subsequent purification by distillation or the like usually will provide a substantially pure product. Also, of importance in the present process is the substantial preservation of optical purity in the β-phellandrene product of an optically active sulfonate salt fed to the process.

It should be noted that the present process can be practiced successfully under basic conditions, i.e. under non-acidic conditions. Thus, to the feed sulfonate salt can be added suitable bases such as, for example, alkali metal and alkaline earth metal hydroxides, oxides, or salts such as carbonates, bicarbonates, acetates, formates, oxylates and the like. Further, organic bases such as an alkali metal pinanoxide can be used (the alkali metal pinanoxides are disclosed in commonly assigned application Ser. No. 879,127 attorney's docket I-2470, of Bernard J. Kane). By non-acidic conditions is meant that no acid is added to the reaction mixture. Thus, the reaction mixture of sulfonate salt does not measure acidic conventionally if such mixture has a pKa of greater than about 16 (see "A Guidebook to Meachnism in Organic Chemistry" by P. Sykes, pages 52–64, John Wiley & Sons, N.Y., N.Y., 1969). While the process, perhaps, may proceed under slightly acid conditions, loss of product β-phellandrene to its isomers may result if acidic conditions prevail in the reaction mixture. Hence, neutral to basic conditions are maintained in the process.

The following examples show in detail how the present invention can be practiced but should not be construed as limiting. In this application, all temperatures are in degrees Centigrade and all percentages are weight percentages, unless otherwise expressly noted.

EXAMPLE 1

Into a 1-liter distillation vessel was charged 3 grams of (+)para-menth-1-ene-7-sulfonic acid sodium salt. The sodium sulfonate salt was heated to 260° C under reduced pressure (22 mm. Hg) for about 15 minutes. After the initial removal of water from the vessel by distillation, a yellow liquid was distilled from the vessel and collected in the distillation flask. This yellow liquid was extracted with ether and the extract dried over magnesium sulfate. GLC analysis of the extract (0.7 gms) showed the ether (89%) and one major component which was identified GC MS and IR as (−) β-phellandrene (9.4%). Minor amounts of α-terpinene and α-phellandrene were noted in the extract also.

EXAMPLE 2

The procedure of Example 1 was repeated with 50 grams of the sodium sulfonate salt to which was added 22 grams of sodium carbonate. Evaporation of the ethereal extract yielded a yellow oil which contained ether (25.4%) and (−)β-phellandrene (60.2%). The theory yield of product, thus, was 52%. The (−)β-phellandrene then was purified by distillation. $[\alpha]_D = -11.01°$.

EXAMPLE 3

The procedure of Example 1 was repeated with 3 grams of the sodium sulfonate salt and 20 grams of NaOH. The yellow oil collected (1.3 grams) analyzed by GLC to be mostly (about 85%) the desired (−)β-phellandrene product.

The results of Examples 2 and 3 show that while the present process can be conducted effectively under basic conditions.

We claim:

1. A process for making β-phellandrene comprising: heating a para-menth-1-ene-7-sulfonate salt at about 150° to about 350° C under non-acidic conditions until said β-phellandrene is formed.

2. The process of claim 1 wherein said heating is done at reduced pressure.

3. The process of claim 1 wherein said heating is done at atmospheric pressure.

4. The process of claim 1 wherein said para-menth-1-ene sulfonate salt is optically active and said β-phellandrene retains substantially the same optical purity as said sulfonate salt.

5. The process of claim 1 wherein said sulfonate salt is a salt of an alkali metal, an alkaline earth metal, ammonia, an amine, aluminum or zinc.

6. The process of claim 5 wherein said salt is of an alkali metal.

7. The process of claim 6 wherein said alkali metal is sodium or potassium.

8. The process of claim 1 wherein said heating is done in the presence of a base.

9. The process of claim 8 wherein said base is an alkali metal oxide, hydroxide, or salt.

10. The process of claim 1 wherein said β-phellandrene is recovered.

11. The process of claim 2 wherein said sulfonate salt is a hydrate.

* * * * *

UNITED STATES PATENT AND TRADEMARK OFFICE
CERTIFICATE OF CORRECTION

PATENT NO. : 4,136,126
DATED : Jan. 23, 1979
INVENTOR(S) : Linda M. Hirschy, Bernard J. Kane, and Sean G. Traynor It is certified that error appears in the above-identified patent and that said Letters Patent are hereby corrected as shown below:

Column 2, l. 32, delete "Ser. No. 879,127".

Signed and Sealed this

Twenty-first Day of April 1981

[SEAL]

Attest:

RENE D. TEGTMEYER

Attesting Officer     Acting Commissioner of Patents and Trademarks